United States Patent [19]
Ott et al.

[11] Patent Number: 6,028,682
[45] Date of Patent: Feb. 22, 2000

[54] SCANNING DEVICE FOR PIXEL-BY-PIXEL PHOTOELECTRIC MEASUREMENT OF A MEASURED OBJECT

[75] Inventors: Hans Ott, Regensdorf; Kurt Ruegg, Effretikon, both of Switzerland

[73] Assignee: Heidelberger Druckmaschinen AG, Heidelberg, Germany

[21] Appl. No.: 08/985,486

[22] Filed: Dec. 4, 1997

[30] Foreign Application Priority Data

Dec. 4, 1996 [DE] Germany .................... 196 50 223

[51] Int. Cl.[7] .................... H04N 1/024; H04N 1/04
[52] U.S. Cl. .................... 358/497; 358/473; 358/484
[58] Field of Search .................... 358/497, 474, 358/473, 494, 484, 475; 382/315, 314, 313

[56] References Cited

U.S. PATENT DOCUMENTS

| | | | |
|---|---|---|---|
| 5,446,559 | 8/1995 | Birk | 358/497 |
| 5,675,411 | 10/1997 | Brooks et al | 356/328 |
| 5,737,096 | 4/1998 | Takeuchi et al. | 358/475 |
| 5,767,980 | 6/1998 | Wang et al. | 358/298 |
| 5,857,133 | 1/1999 | Sun | 358/497 |

*Primary Examiner*—Joseph Mancuso
*Assistant Examiner*—Hien Truong
*Attorney, Agent, or Firm*—Tarolli, Sundheim, Covell Tummino & Szabo L.L.P.

[57] ABSTRACT

The scanning device comprises a measuring table (T) to which measured object B can be fixed for measurement, measurement carriage (W) with a photoelectric scanning device (100) which can be linearly moved over the surface of the measuring table by means of a drive unit (A), a control unit (S) for the measuring carriage (W), the scanning device (100) and the drive unit (A), and a processing unit (C) for processing and analyzing the measuring signals generated by scanning device (100) from scanned pixels (8) of measured object (B). Scanning device (100) in turn comprises a plurality of measuring heads (120) for pixel-by-pixel measurement of a corresponding plurality of pixels (8) of measured object (B) lying in a row one behind the other and along a corresponding plurality of scanning tracks (5a, 5b) which are parallel to motion direction (X) of measuring carriage (W) such that measured object (B) is sequentially scanned, pixel by pixel, in a grid-like scanning pattern.

6 Claims, 5 Drawing Sheets

SCANNING DEVICE FOR PIXEL-BY-PIXEL PHOTOELECTRIC MEASUREMENT OF A MEASURED OBJECT

The invention relates to a scanning device for pixel-by-pixel photoelectric measurement of a measured object, particularly a printed sheet preferably printed in multiple colors, in accordance with the preamble of the independent claim.

Scanning devices of this type are generally referred to as Òscanners.6 A first known type of conventional scanners is provided with a single measuring head that can be moved in one or two dimensions relative to the measured object. In case of one-dimensional mobility of the measuring head, the measured object can be moved in the other dimension. The measuring head photoelectrically scans a small area of the measured object at a time which is referred to as a pixel. Each pixel to be scanned is individually approached by a corresponding motion of the measuring head or the measured object. Scanning is generally densitometric but there are also known scanners with colorimetric or spectral measuring heads. A substantial disadvantage of these known scanners is the time required to completely scan a standard sized printed sheet by individually approaching the pixels. As a rule, such scanners are therefore unsuitable for use with automatically controlled modern printing machines.

Another known type of scanners, thus far operating exclusively densitometrically, has a stationary linear arrangement of a plurality of measuring heads enabling simultaneous or sequential scanning of an entire line of pixels of the measured object. To measure additional pixel lines, the measured object is moved relative to the measuring head arrangement. Such scanners are used, for instance, on printing machines to measure printed sheets directly during the printing operation. They are not suitable, however, for fully automatic scanning of the entire scanning field of stationary printed sheets.

The object of the present invention is to improve such a generic-type scanning device permitting fully automatic scanning of the entire scanning field of a stationary measured object with adequate resolution and, in particular, including spectral scanning at justifiable design complexity and in a very short time. A further object of the invention is to create the preconditions for continuous scanning in an orthogonal scanning pattern. An additional object of the invention is to obtain adequately high resolution at the lowest possible design complexity. Yet an other object of the invention is to create a simple design that optimally uses the available measuring light for simultaneous measurement of the visible spectral components and the IR components of the measuring light.

These objects of the invention are attained by the inventive scanning device as defined in the independent and the dependent claims.

Details and advantages of the scanning device according to the invention result from the following description of an exemplary embodiment in conjunction with the drawing.

Figure 1:
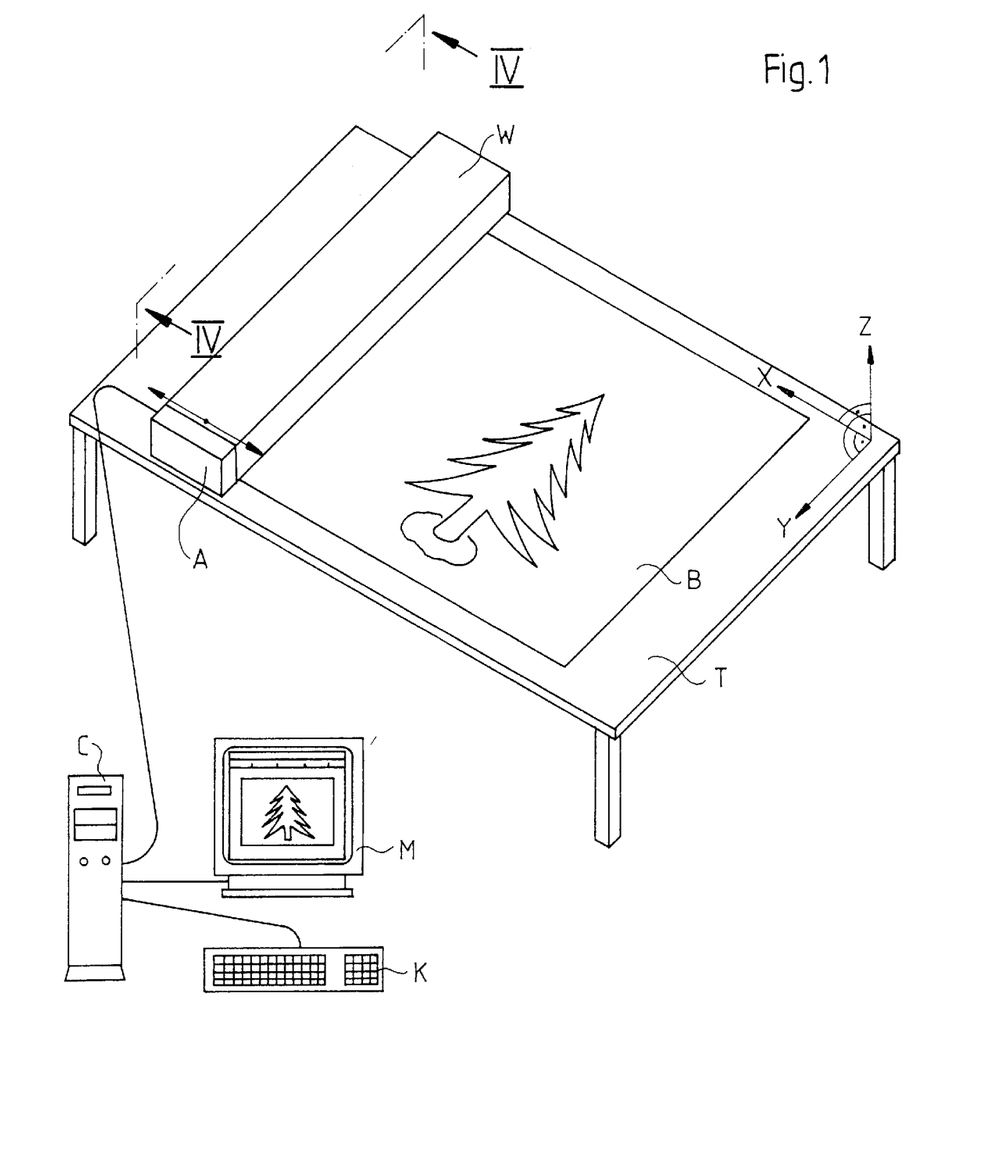
FIG. 1 is a simplified general view of an exemplary embodiment of the scanning device according to the invention.

The general structure of the scanning device according to the invention corresponds to conventional measuring apparatuses which are typically used, for example, in the graphics industry for point-by-point photoelectric measurement of printed sheets taken from the printing process. The scanning device comprises a substructure in the form of a slightly sloping rectangular measuring table T on which the printed sheet to be measured D measured object B D can be positioned. Stops (not shown) are provided for positioning the measured object. Measured object B on measuring table T is preferably fixed electrostatically or by means of known suction mechanisms. A measuring carriage W is arranged on measuring table T, with the actual scanning device (not depicted) being disposed on or in such measuring carriage W. Measuring carriage W extends across the depth of the measuring table in coordinate direction y and is motor drivel so that it can be linearly moved back and forth across the width of the table in coordinate direction x. The corresponding drive and control units are provided in measuring carriage W and on or under measuring table T. In the drawing, the drive mechanism is shown only symbolically by reference symbol A. The scanning device furthermore comprises a processing/unit in the form of a computer C with keyboard K and color monitor M. Computer C interacts with the control unit on measuring table T or in measuring carriage W and processes the measuring signals generated by the scanning device disposed on measuring carriage W.

Figure 2:
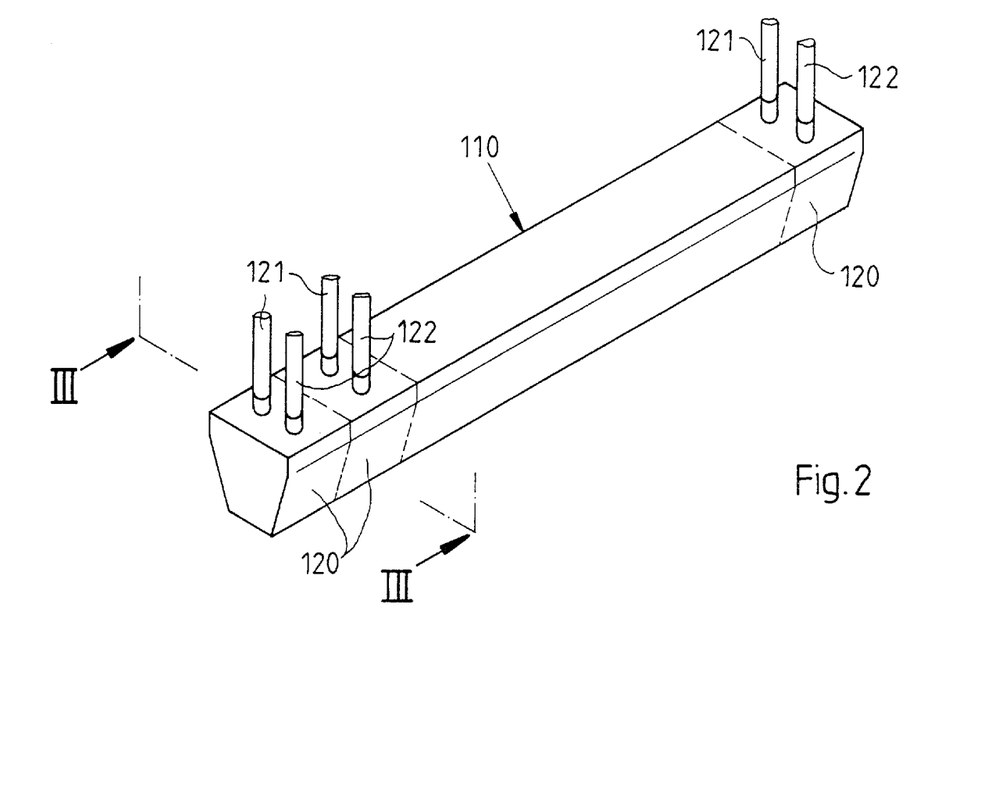
FIG. 2 is a schematic sketch of a measuring head arrangement of the scanning device.
Figure 4:
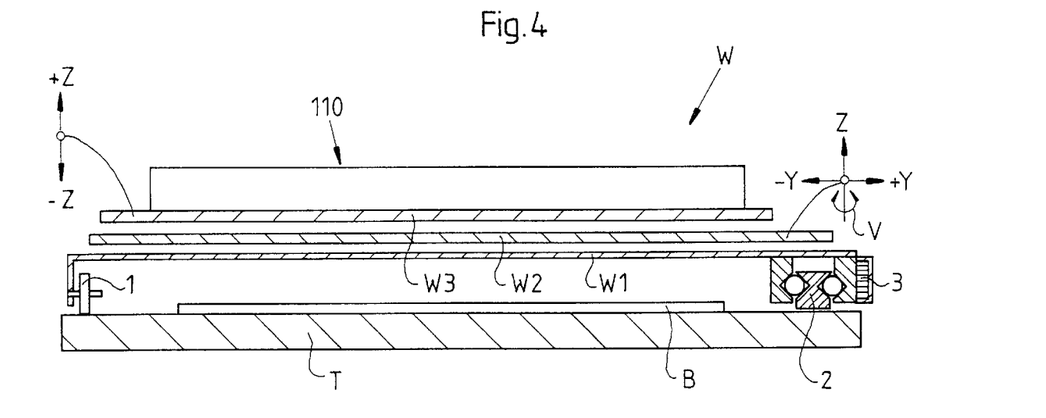
FIG. 4 is a section through the measuring carriage of the scanning device along the plane indicated by Lines IV—IV in FIG. 1.
Figure 5:
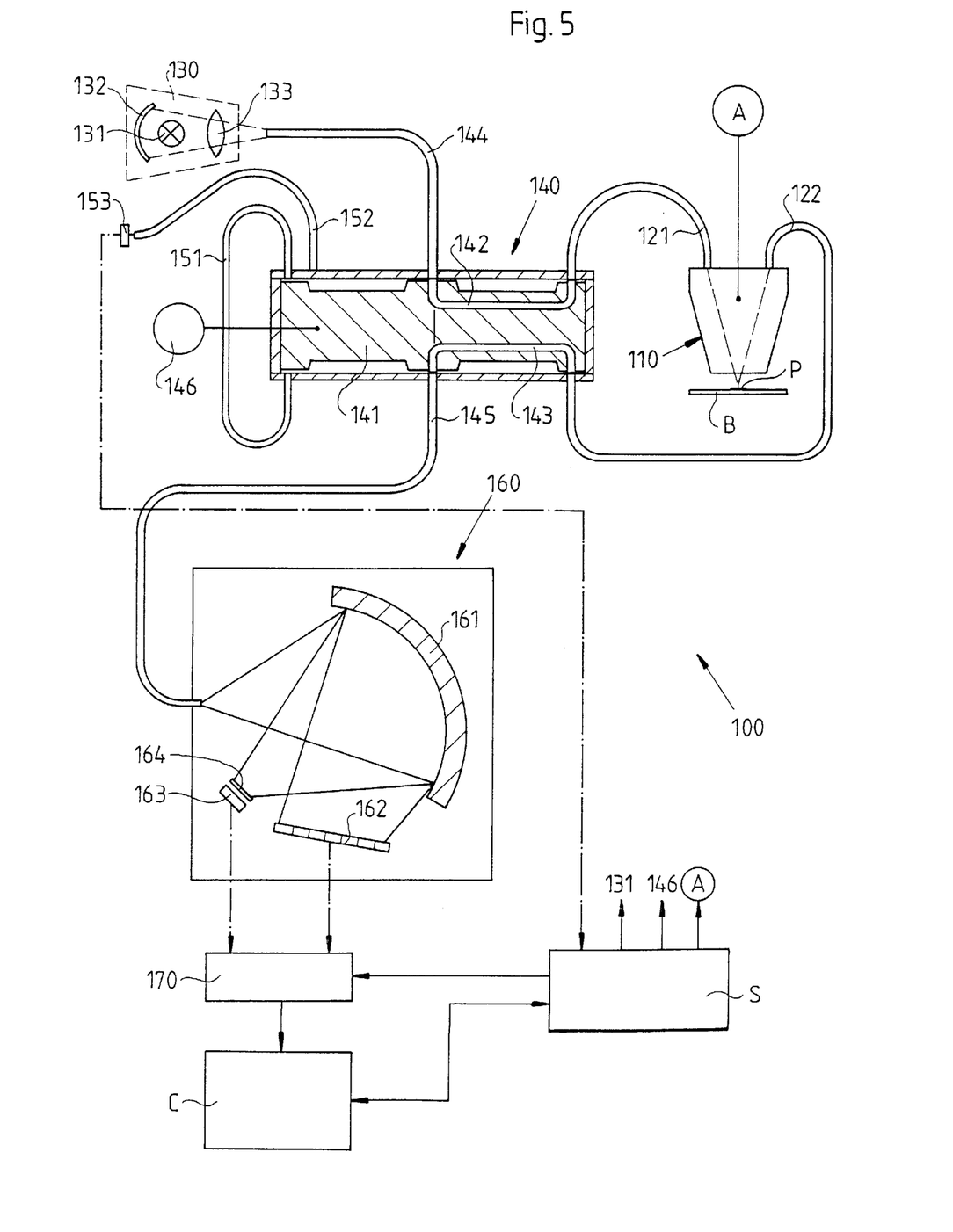
FIG. 5 is a schematic representation of the scanning device.

Measuring carriage W comprises the actual scanning device 100 which is described in further detail below and, in accordance with FIGS. 2 and 5, essentially comprises an approximately beam-shaped measuring head arrangement 110 having a plurality of measuring heads 120, a light source 130, a light distribution unit 140 and a receiver unit 160. As shown in FIG. 4, measuring carriage w essentially comprises three approximately trough-shaped support elements W1, W2 and W3 which are mounted adjacent to or on top of each other and are arranged such that they are mobile relative to each other. Measuring head arrangement 110 is mounted on the third and topmost support element W3. All the other components of the scanning device are disposed on the first and lowest support element W1 which is not shown in further detail in FIG. 4. The first and lowest support element W1 is arranged in a plane parallel to measuring table T such that it can be moved linearly back and forth across the width of measuring table T. Thus, first support element W1 can move in the direction of the x axis (FIG. 1). This direction, independent of its sign, is hereinafter referred to as second direction x. Second support element W2 is mounted on top of first support element W1. Relative to element W1, second support element W2 on the one hand can be parallel displaced in the direction of the y axis in a plane parallel to measuring table T and on the other hand can be swung around the z axis, which is perpendicular to the plane of the measuring table (see also FIG. 1), between two angular positions in swing motion direction v. The y motion direction of the second support element, independent of its sign, is hereinafter referred to as first direction y. Finally, third support element W3 is mounted on second support element W2 and can be adjusted relative to element W2 in the direction of the z axis, in other words, with respect to its height relative to the surface of measuring table T. As furthermore shown in FIG. 4, first support element W1, and thus the entire measuring carriage W, is supported at its lower end on rollers 1 and guided at its upper end in rail 2 mounted on measuring table T and fixed to a motor-driven transport belt 3 pulling first support element W1 and thus the entire measuring carriage W back and forth in transverse direction across the measuring table. Transport belt 3 forms part of drive unit A.

Beam-shaped measuring head arrangement 110 is oriented parallel to the longitudinal direction of measuring carriage W and, based on its arrangement on the third and topmost support element W3 of measuring carriage W, has four degrees of freedom of movement: linear movement between a start and a stop position forward and backward in second direction (x axis), linear parallel displacement upward and downward in first direction (y axis), height adjustment relative to measuring table T (z coordinate, height h) and swingability around the z axis between a first and a second angular position (swing direction v). The motion of measuring head arrangement 110 corresponding to its four degrees of freedom is effected by the aforementioned drive unit A in conjunction with control unit S (FIG. 5) which in turn receives higher-level control commands from computer C.

Figure 3:
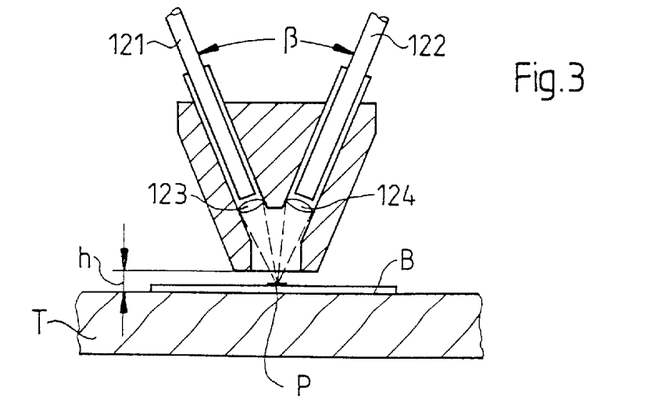
FIG. 3 is a section through a measuring head of the measuring head arrangement along the plane indicated by Lines III—III in FIG. 2.
Figure 6:
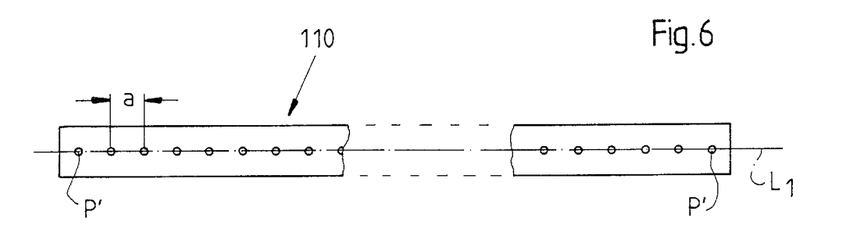
FIG. 6 is a simplified bottom view of the measuring head arrangement.

Beam-shaped measuring head arrangement 110 is disposed on measuring carriage W at a short distance above measured object B and comprises a plurality n (typically 160) of measuring heads 120 which are combined into a beam-shaped block. Such measuring heads 120 are provided, respectively, with an incoming light guide 121 and an outgoing light guide 122 which are arranged such that they apply illuminating light to measured object B in strictly limited areas of approximately 2–3 mm diameter or, respectively, remove the measuring light reflected from these areas (FIGS. 2 and 3). The arrangement is such that the returned measuring light is captured at an approximately $45_i$ angle β to the light application direction. Within individual measuring heads 120 there are optical elements 123 and 124 which suitably focus on the areas the illuminating light supplied by incoming light guides 121 and inject the light returned from these areas into outgoing light guides 122. Such optical elements 123 and 124 can be conventional optical lenses or graded-index elements. The areas of measured object B measured by measuring heads 120 are hereinafter referred to as pixels P of measured object B. The projections of such pixels P in the direction of the z axis onto the measuring head arrangement 110 or measuring heads 120, that is, the measuring positions relative to the measuring head arrangement, are referred to as PÕ. The arrangement of measuring heads 120 is such that measuring positions PÕ lie in a straight line $L_1$ and at equal distance a with respect to each other (FIG. 6).

Incoming and outgoing light guides 121 and 122, respectively, of measuring heads 120 are connected with the substantially drum-shaped light distribution unit 140 and open out equidistantly along two circular lines in said distribution unit 140. For clarityõs sake, as shown in FIG. 5, light guides 121 and 122, respectively, open out on opposite end faces into light distributing unit 140. In practice, such openings of light guides 121, 122 are on the same end face along two concentric circles. on the interior of light distributing unit 140 there is a rotor 141 uniformly driven by motor 146. Such rotor comprises two light guide bridges 142 and 143, one of which, 142, optically connects during its rotation an axially joining light supply guide 144 successively with incoming light guides 121 and the other, 143, optically connects an axially joining light removal guide 145 successively with outgoing light guides 122. The individual connections are made cyclically and the respective incoming and outgoing light guides 121 and 120 pertaining to the same measuring head 120 are simultaneously connected with light supply guide 144 and light removal guide 145, respectively. Furthermore, light guides 121 and 122 are arranged such that the individual measuring heads 120 of measuring head arrangement 110 are activated sequentially, that is, cyclically one after the other.

Light supply guide 144 is connected with light source 130. Light source 130 comprises a xenon lamp 131, possibly a concave mirror 132 and a lens system 133 which injects the illuminating light coming from lamp 131 into light guide 144. Light distributing unit 140 cyclically and sequentially connects the individual measuring heads 120 with the light source 130. Each measuring head 120, respectively, receives the entire available illuminating light such that the intensity of the illuminating light is not split among the individual measuring heads 120. This makes it possible to keep the wattage of light source 130 relatively low.

Light removal guide 145 is connected with receiving unit 160 such that the latter, too, is cyclically sequentially connected with the individual measuring heads 120 via light distributing unit 140. Receiving unit 160 is made as a spectrophotometer and comprises, as its dispersive element, a concave holographic reflection diffraction grating 161 as well as a photoelectric transducer line 162 in the form, for instance, of a linear CCD field or photodiode field as transducer. Transducer line 162 is disposed in the region of the interference maxima of the first order generated by dispersive element 161. The individual transducer elements of the transducer line are respectively charged with only a relatively narrow spectral range, e.g. 10D20 nm, of the visible component of the measuring light.

Moreover, receiving unit 160, according to a further essential aspect of the invention, comprises an additional opto-receiver 163 which, in contrast to transducer line 162, is not disposed in the region of the diffraction maxima of the first order but in the region of the diffraction maxima of the zeroth order and, for example, by means of an upstream filter 164, is sensitized to a selected wavelength range in the region of the infrared component of the measuring light. The additional opto-receiver 163 and its special arrangement in the region of the diffraction maxima of the zeroth order keeps low the design complexity for a measurement both in the visible as well as in the IR range of the spectrum and simultaneously utilizes the measuring light in an optimal manner.

Downstream from transducer line 162 and additional opto-receiver 163, an amplifier and A/D converter 170 is disposed for converting the measuring signals which are generated by transducer line 162 and additional opto-receiver 163 and correspond to the returned measuring light into a form that can be processed by the downstream processing unit, here in the form of computer C. The measuring signals generated by transducer line 162 and representing the visible spectral components of the measuring light are hereinafter referred to as spectral measuring signals, those generated by IR opto-receiver 163 and representing the infrared component of the measuring light are referred to as IR measuring signals.

According to a further advantageous embodiment of the invention, light distributing unit 140 has a number greater by 3 of inputs and outputs than the number n of measuring heads 120 or incoming and outgoing light guides 121 and 122 associated therewith. One of these additional inputs is connected directly, that is, without the detour via a measuring head 120, with the associated output by means of a calibration light guide 151 such that in the corresponding position of rotor 141, light source 130 is directly connected, once per rotation, with receiver unit 160. The correspondingly generated measuring signals can be analyzed by control unit S or processing unit C to calibrate scanning device 100. Connected to the other input of light distributing unit 140 is a synchronizing light guide 152 which leads to an additional light sensor 153 that is connected to control unit S. Light sensor 153, once per rotation of rotor 141, is directly connected with light source 130. The signal thus generated can be analyzed by control unit S or processing unit C to synchronize scanning unit 100. A third output is associated with an unused input (that is, one that is not charged with light) and serves for the dark calibration of the measuring system.

The functioning of the above described scanning device is explained below. All functional sequences are assumed to be controlled by computer C in conjunction with control unit S.

First, scanning device 100 is adjusted to the thickness of measured object B. For this purpose, measuring carriage W is driven over measured object B until measuring heads 120 are located in the border area of measured object B. Now, measured object B is initially scanned while measuring carriage W is stationary with the measuring heads 120 at various heights h over measuring table T. Height h is adjusted until the generated measuring signals reach their maximum value. Height adjustment h determined in this manner is stored until another measured object B is scanned. The height is automatically adjusted by a height adjustment device formed by drive unit A in conjunction with control unit S and computer C.

Now, measured object B is actually scanned pixel-by-pixel in two passes, once while measuring carriage W moves forward from its start position on the left of measured object B to its end position on the right of measured object B and once while measuring carriage W returns to its start position.

Figure 7:
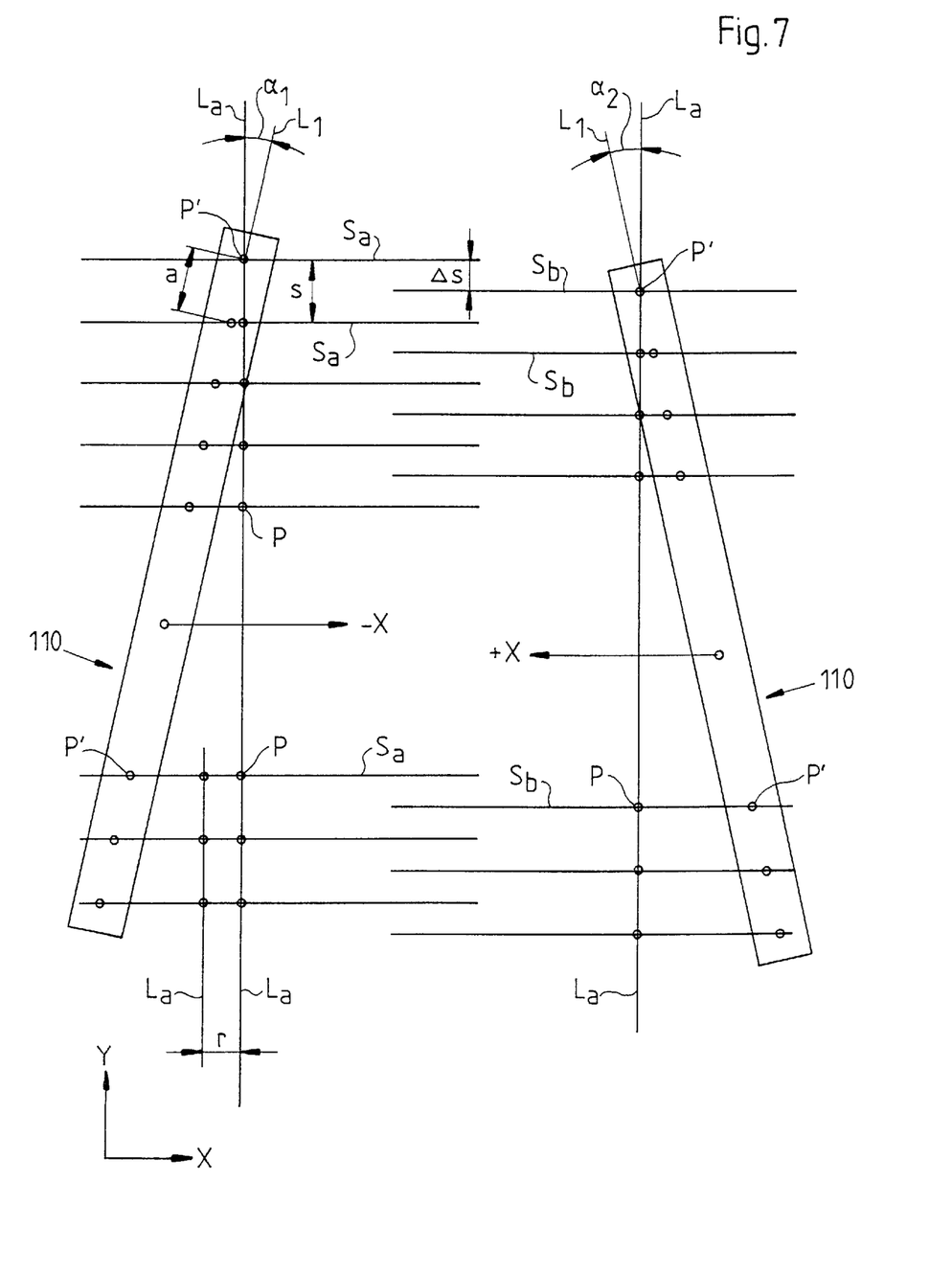
FIG. 7 is a sketch illustrating the scanning process and the motions of the measuring head arrangement during scanning.

As shown in FIG. 7, pixel-by-pixel scanning is two-dimensional: the sequential activation of measuring heads 120 arranged one behind the other along a line $L_1$ causes scanning along scanning lines $L_a$ which are substantially parallel to first direction y. The linear movement of measuring carriage W and thus measuring heads 120 in second direction x causes each measuring head 120 to scan measured object B along first and second scanning track $S_a$ and $S_b$, respectively, which are parallel to the motion direction (second direction x) of measuring carriage W. Thus, scanning lines $L_a$ and first and second scanning tracks $S_a$ and $S_b$ form a grid-shaped scanning pattern with scanned pixels P located at the grid crossing points. Division of the scanning field into individual pixels P is ensured by the distance between measuring heads 120 and by their sequential activation over time. Distances s of the individual tracks $S_a$ and $S_b$, respectively, are determined by distances a of measuring heads 120. Distances r between two successive scanning lines $L_a$ result from cycle time t required for one full rotation by the rotor of light distributing unit 140 and from feed rate u of measuring carriage W in direction x. The measurement positions on measuring head arrangement 110 which are determined by the arrangement of measuring heads 120 are identified as PÕ.

If measuring heads 120 were disposed along a line parallel to first direction y, this would result in scanning lines $L_a$ being sloped with respect to first direction y due to the feed movement of measuring carriage W during scanning. In other words, the scanning pattern would not be orthogonal. This would make the analysis of the measuring signals substantially more difficult. An orthogonal scanning pattern could theoretically be achieved by stopping measuring carriage W during scanning along a scanning line. In practice, however, this is not advantageous for a number of reasons. In particular, the entire scanning process would take an undesirable amount of time. Furthermore, the incremental motion of measuring carriage W is mechanically undesirable. To obtain an orthogonal scanning pattern despite a continuously moving measuring carriage W, an essential aspect of the invention provides that measuring head arrangement 110 during feed is inclined by a correction angle $\alpha_1$ or $\alpha_2$ to first direction x. Such inclination is obtained by swinging second support element W2 around a swing axis that is parallel to the z axis, which swing axis extends through measuring position PÕ of the first measuring head 120 of measuring head arrangement 110 activated during a scanning cycle. Correction angle $\alpha_1$ or $\alpha_2$ is selected such that, at the time of activation of the respective measuring head 120, measuring position PÕ of the last measuring head 120 to be activated during a scanning cycle is located exactly on scanning line $L_a$ on which the first measuring head 120 was located during the same scanning cycle at the time of its activation. As measuring carriage W returns, the inclination of measuring head arrangement 110 is in mirror image to first direction x which determines the direction of scanning line $L_a$. The two correction angles $\alpha_1$ and $\alpha_2$ are identical in size but have opposite signs.

The obtainable resolution in direction y depends on the number of measuring heads 120. To obtain a scanning resolution that is suitable for practical purposes with a number of measuring heads 120 at a justifiable complexity, another essential aspect of the invention provides that as measuring carriage W returns in the first direction, measuring head arrangement 110 is parallel offset by a small distance Δs such that scanning tracks $S_b$ created during the return are positioned exactly in the center between scanning tracks $S_a$ of the first sweep. If several back and forth sweeps are acceptable, the resolution can be substantially increased by a corresponding offset of measuring head arrangement 110 at each individual sweep by a fraction of the normal track distance s.

Correction angles $\alpha_1$ and $\alpha_2$ are linked to the desired resolution ax in second direction x, the number n and the distances a of measuring heads 120, the total number k*n of the scanning tracks, the cycle time t of the light distributing unit 140, the number m of additional positions of light distributing unit 140 not connected with measuring heads 120, and the feed rate u of measuring head arrangement 110 in second direction x. Based on a square scanning pattern, wherein resolution ax in direction x and resolution ay in direction y are approximately 2.5 mm each, and with a single back and forth sweep of measuring carriage W, wherein the total number k*n of scanning tracks 5a, 5b equal twice the number of measuring heads 120, the resulting value of correction angles $\alpha_1$ and $\alpha_2$ is approximately $0.15_i$.

The described scanning device 100 according to the invention, at a justifiable design complexity, permits rapid and efficient pixel-by-pixel calorimetric measurement of colored printed sheets B with adequate resolution over the entire surface of printed sheets B, that is, measurement in the scanning field as opposed to linear measurement of printed color control scales. The measuring data thus obtained can then be processed according to various criteria for automatic control of the printing process.

We claim:

1. Scanning device for pixel-by-pixel photoelectric measurement of a measured object, particularly a printed sheet preferably printed in multiple colors, with a measuring table on which a measured object, can be fixed for measurement, with a scanning device which can be moved over the surface of said measured object and which photoelectrically scans at least one pixel of said measured object, respectively, with a drive unit that moves said scanning device over the measured object such that all pixels of said measured object can be measured with a control unit for said scanning device and said drive unit, and with a processing unit for processing and analyzing the measuring signals generated by said scanning device from said scanned pixels of said measured object, characterized in that said scanning device comprises a plurality of measuring heads for pixel-by-pixel measurement of a corresponding plurality of said pixels of said measured object lying substantially in a row one behind the other in a first direction (y) and that said measuring heads are arranged such that they can be collectively moved in a second direction (x) which extends substantially transversely to first direction (y) such that said measured object can be scanned in a plurality of first scanning tracks ($S_a$) which are parallel to said second direction (x), said scanning device cyclically sequentially activates said measuring heads, said measuring heads scan said measured object as they collectively move along scanning tracks ($S_a$, $S_b$) and are arranged substantially along a straight line ($L_1$) which is inclined to said first direction (y) by a correction angle ($\alpha_1$) such that the pixels of said measured object, scanned during a scanning cycle lie along a scanning line ($L_a$) which is parallel to said first direction (y).

2. Scanning device for pixel-by-pixel photoelectric measurement of a measured object, particularly a printed sheet preferably printed in multiple colors, with a measuring table on which a measured object, can be fixed for measurement, with a scanning device which can be moved over the surface of said measured object and which photoelectrically scans at least one pixel of said measured object, respectively, with a drive unit that moves said scanning device over the measured object such that all pixels of said measured object can be measured with a control unit for said scanning device and said drive unit, and with a processing unit for processing and analyzing the measuring signals generated by said scanning device from said scanned pixels of said measured object, characterized in that said scanning device comprises a plurality of measuring heads for pixel-by-pixel measurement of a corresponding plurality of said pixels of said measured object lying substantially in a row one behind the other in a first direction (y) and that said measuring heads are arranged such that they can be collectively moved in a second direction (x) which extends substantially transversely to first direction (y) such that said measured object can be scanned in a plurality of first scanning tracks ($S_a$) which are parallel to said second direction (x), said measuring heads can be collectively offset parallel to said first direction (y) by said drive unit such that said measured object can be scanned in a plurality of second scanning tracks ($S_b$) which are parallel offset to first scanning tracks ($S_a$), said scanning device scans said measured object during a forward motion of said measuring heads from a start position to an end position along said first scanning track ($S_a$) and during a reverse motion of the measuring heads from the end position to the start position along said second scanning tracks ($S_b$), said measuring heads, by means of said drive unit, can be collectively swung in a plane parallel to said measuring table, between a first and a second angular position ($\alpha_1$, $\alpha_2$), said drive unit swings said measuring heads into the first angular position ($\alpha_1$) as they move forward and into said second angular position ($\alpha_2$) as they return and the line ($L_1$), along which measuring heads are disposed, is inclined in the two angular positions ($\alpha_1$, $\alpha_2$) in mirror image to first direction (y).

3. Scanning device for pixel-by-pixel photoelectric measurement of a measured object, particularly a printed sheet preferably printed in multiple colors, with a measuring table on which a measured object, can be fixed for measurement, with a scanning device which can be moved over the surface of said measured object and which photoelectrically scans at least one pixel of said measured object, respectively, with a drive unit that moves said scanning device over the measured object such that all pixels of said measured object can be measured with a control unit for said scanning device and said drive unit, and with a processing unit for processing and analyzing the measuring signals generated by said scanning device from said scanned pixels of said measured object, characterized in that said scanning device comprises a plurality of measuring heads for pixel-by-pixel measurement of a corresponding plurality of said pixels of said measured object lying substantially in a row one behind the other in a first direction (y) and that said measuring heads are arranged such that they can be collectively moved in a second direction (x) which extends substantially transversely to first direction (y) such that said measured object can be scanned in a plurality of first scanning tracks ($S_a$) which are parallel to said second direction (x), said scanning device cyclically sequentially activates said measuring heads, said measuring heads scan said measured object as they collectively move along scanning tracks ($S_a$, $S_b$) and are arranged substantially along a straight line ($L_1$) which is inclined to first direction (y) by a corrections angle ($\alpha_1$) such that the pixels of said measured object, scanned during a scanning cycle lie along a scanning line ($L_a$) which is parallel to first direction (y), said measuring heads, by means of a drive unit, can be collectively swung in a plane parallel to said measuring table, between a first and a second angular position ($\alpha_1$, $\alpha_2$), said drive unit swings said measuring heads into the first angular position ($\alpha_1$) as they move forward and into the second angular position ($\alpha_2$) as they return and the line ($L_1$), along which said measuring heads are disposed, is inclined in the two angular positions ($\alpha_1$, $\alpha_2$) in mirror image to said first direction (y).

4. Scanning device for pixel-by-pixel photoelectric measurement of a measured object, particularly a printed sheet preferably printed in multiple colors, with a measuring table on which a measured object, can be fixed for measurement, with a scanning device which can be moved over the surface of said measured object and which photoelectrically scans at least one pixel of said measured object, respectively, with a drive unit that moves said scanning device over the measured object such that all pixels of said measured object can be measured with a control unit for said scanning device and said drive unit, and with a processing unit for processing and analyzing the measuring signals generated by said scanning device from said scanned pixels of said measured object, characterized in that said scanning device comprises a plurality of measuring heads for pixel-by-pixel measurement of a corresponding plurality of said pixels of said measured object lying substantially in a row one behind the other in a first direction (y) and that said measuring heads are arranged such that they can be collectively moved in a second direction (x) which extends substantially transversely to first direction (y) such that said measured object can be scanned in a plurality of first scanning tracks ($S_a$)

which are parallel to said second direction (x), said measuring heads can be collectively offset parallel to said first direction (y) by said drive unit such that said measured object can be scanned in a plurality of second scanning tracks ($S_b$) which are parallel offset to first scanning tracks ($S_a$), said device characterized in that a measuring carriage comprises three support elements, wherein a first support element can be moved in a plane parallel to the measuring table a second direction (x) relative to said measuring table, a second support element mounted on said first support element can be parallel offset relative to said first support element in a plane parallel to said measuring table in said first direction (y) as well as swung between the two angular positions ($\alpha_1$, $\alpha_2$), and a third support element mounted on said second support element can be adjusted in relation to said second support element in a direction that is perpendicular to said measuring table and that such third support element carries said measuring heads.

5. Scanning device for pixel-by-pixel photoelectric measurement of a measured object, particularly a printed sheet preferably printed in multiple colors, with a measuring table on which a measured object, can be fixed for measurement, with a scanning device which can be moved over the surface of said measured object and which photoelectrically scans at least one pixel of said measured object, respectively, with a drive unit that moves said scanning device over the measured object such that all pixels of said measured object can be measured with a control unit for said scanning device and said drive unit, and with a processing unit for processing and analyzing the measuring signals generated by said scanning device from said scanned pixels of said measured object, characterized in that said scanning device comprises a plurality of measuring heads for pixel-by-pixel measurement of a corresponding plurality of said pixels of said measured object lying substantially in a row one behind the other in a first direction (y) and that said measuring heads are arranged such that they can be collectively moved in a second direction (x) which extends substantially transversely to first direction (y) such that said measured object can be scanned in a plurality of first scanning tracks ($S_a$) which are parallel to said second direction (x), said measuring heads are provided, respectively, with a light guide supplying an illuminating light to said measured object and a light guide removing the measuring light reflected by said measured object, that said scanning device has a light source, a receiver unit and a light distribution unit, which light distribution unit cyclically, sequentially connects, respectively, the incoming light guide and the outgoing light guide of the individual measuring heads with, respectively, light source and receiver unit, said light distribution unit has two synchronously rotating light guide bridges which optically connect, respectively, an axially disposed light guide in cyclical sequential manner with a plurality of peripherally disposed light guides, said receiver unit is made as a spectrophotometer which separates the measured light supplied to it by said measuring heads from said scanned pixels of said measured object into a predefined number of narrow band spectral regions in the range of the visible spectrum and converts them to corresponding electrical spectral measuring signals, a receiver unit is further provided with an opto-receiver for selectively measuring at least a partial area of the infrared component of the measuring light and for generating a corresponding electrical IR measuring signal, said receiver unit has a concave reflection diffraction grating as a dispersive element and a photoelectric transducer line disposed in the region of the interference maxima of the first order generated by such reflection diffraction grating and that opto-receiver for the IR component of the measuring light is disposed in the region of the interference maximum of the zeroth order of diffraction grating.

6. Scanning device for pixel-by-pixel photoelectric measurement of a measured object, particularly a printed sheet preferably printed in multiple colors, with a measuring table on which a measured object, can be fixed for measurement, with a scanning device which can be moved over the surface of said measured object and which photoelectrically scans at least one pixel of said measured object, respectively, with a drive unit that moves said scanning device over the measured object such that all pixels of said measured object can be measured with a control unit for said scanning device and said drive unit, and with a processing unit for processing and analyzing the measuring signals generated by said scanning device from said scanned pixels of said measured object, characterized in that said scanning device comprises a plurality of measuring heads for pixel-by-pixel measurement of a corresponding plurality of said pixels of said measured object lying substantially in a row one behind the other in a first direction (y) and that said measuring heads are arranged such that they can be collectively moved in a second direction (x) which extends substantially transversely to first direction (y) such that said measured object can be scanned in a plurality of first scanning tracks ($S_a$) which are parallel to said second direction (x), said measuring heads are provided, respectively, with a light guide supplying an illuminating light to said measured object and a light guide removing the measuring light reflected by said measured object, that said scanning device has a light source, a receiver unit and a light distribution unit, which light distribution unit cyclically, sequentially connects, respectively, the incoming light guide and the outgoing light guide of the individual measuring heads with, respectively, light source and receiver unit, said light distribution unit has two synchronously rotating light guide bridges which optically connect, respectively, an axially disposed light guide in cyclical sequential manner with a plurality of peripherally disposed light guides.

* * * * *